United States Patent
Konya (10) Patent No.: US 12,082,928 B2
(45) Date of Patent: *Sep. 10, 2024

(54) MEDICAL SYSTEM AND METHOD OF MANUFACTURING THEREOF

(71) Applicant: Roche Diabetes Care, Inc., Indianapolis, IN (US)

(72) Inventor: Ahmet Konya, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,778

(22) Filed: Aug. 4, 2023

(65) Prior Publication Data

US 2023/0397854 A1    Dec. 14, 2023

Related U.S. Application Data

(63) Continuation of application No. 16/898,049, filed on Jun. 10, 2020, which is a continuation of application No. PCT/EP2018/086139, filed on Dec. 20, 2018.

(30) Foreign Application Priority Data

Dec. 21, 2017 (EP) .................................... 17209756

(51) Int. Cl.
*A61B 5/1486* (2006.01)
*A61B 5/00* (2006.01)

(52) U.S. Cl.
CPC ........ *A61B 5/14865* (2013.01); *A61B 5/6832* (2013.01); *A61B 2560/0214* (2013.01);
(Continued)

(58) Field of Classification Search
CPC .............. A61B 5/14865; A61B 5/6832; A61B 2560/0214; A61B 2560/0456;
(Continued)

(56) References Cited

U.S. PATENT DOCUMENTS 5,413,690 A    5/1995 Kost et al.
5,762,770 A    6/1998 Pritchard et al.
(Continued)

FOREIGN PATENT DOCUMENTS

CN    1703254 A    11/2005
CN    1976627 A    6/2007
(Continued)

OTHER PUBLICATIONS

International Preliminary Report on Patentability, PCT/EP2018/086139, Nov. 18, 2019, 5 pages.
(Continued)

*Primary Examiner* — David J. McCrosky
*Assistant Examiner* — Clarissa Cuevas
(74) *Attorney, Agent, or Firm* — Bose McKinney & Evans LLP (57) ABSTRACT

An inventive medical system has a housing with a first guiding surface. A preassembled module is received in the housing. The module includes electronics electrically connected to an analytical sensor, an insertion component configured for inserting the analytical sensor into body tissue of a user and a sterility cap at least partially surrounding the insertion component. The module has a second guiding surface. A protective cap is removably connected to the housing and covers the preassembled module. The protective cap is removable from the housing by pulling the protective cap from the housing. The first guiding surface guides the protective cap during the pulling of the protective cap from the housing and the second guiding surface guides the sterility cap during pulling the sterility cap from the insertion component. The length of the first guiding surface exceeds the length of the second guiding surface.

35 Claims, 1 Drawing Sheet

(52) U.S. Cl.
CPC . *A61B 2560/0456* (2013.01); *A61B 2560/063* (2013.01); *A61B 2562/12* (2013.01); *A61B 2562/242* (2013.01); *A61B 2562/247* (2013.01)

(58) Field of Classification Search
CPC .......... A61B 2560/063; A61B 2562/12; A61B 5/14503; A61B 5/1459; A61B 5/14; A61B 5/73; A61B 5/1451; A61B 5/14524
See application file for complete search history.

(56) References Cited

U.S. PATENT DOCUMENTS

| | | | |
|---|---|---|---|
| 5,798,031 | A | 8/1998 | Charlton et al. |
| 6,129,823 | A | 10/2000 | Hughes et al. |
| 6,256,523 | B1 | 7/2001 | Diab et al. |
| 6,360,888 | B1 | 3/2002 | McIvor et al. |
| 8,577,437 | B2 | 11/2013 | Roesicke et al. |
| 8,721,544 | B2 | 5/2014 | Roesicke et al. |
| 8,764,657 | B2 | 7/2014 | Curry et al. |
| 8,764,857 | B2 | 7/2014 | Mason |
| 9,164,056 | B2 | 10/2015 | Harrison |
| 9,248,232 | B2 | 2/2016 | Yodfat et al. |
| 9,265,453 | B2 | 2/2016 | Curry et al. |
| 9,687,183 | B2 | 6/2017 | Donnay et al. |
| 9,693,713 | B2 | 7/2017 | Pace et al. |
| 9,808,186 | B2 | 11/2017 | Stafford |
| 10,213,139 | B2 | 2/2019 | Rao et al. |
| 11,006,871 | B2 | 5/2021 | Yee et al. |
| 11,179,068 | B2 | 11/2021 | Pace et al. |
| 11,202,591 | B2 | 12/2021 | Yee et al. |
| 2005/0012731 | A1 | 1/2005 | Yamazaki et al. |
| 2005/0013731 | A1 | 1/2005 | Burke et al. |
| 2005/0101912 | A1 | 5/2005 | Faust et al. |
| 2005/0158205 | A1 | 7/2005 | Swanson et al. |
| 2005/0283114 | A1 | 12/2005 | Bresina et al. |
| 2006/0020186 | A1 | 1/2006 | Brister et al. |
| 2007/0073129 | A1 | 3/2007 | Shah et al. |
| 2007/0189928 | A1 | 8/2007 | Sabol |
| 2007/0202488 | A1 | 8/2007 | Hendrix et al. |
| 2008/0027296 | A1 | 1/2008 | Hadvary et al. |
| 2008/0097246 | A1 | 4/2008 | Stafford |
| 2008/0146904 | A1 | 6/2008 | Hunn |
| 2008/0190766 | A1 | 8/2008 | Rush et al. |
| 2008/0234561 | A1 | 9/2008 | Roesicke et al. |
| 2008/0242962 | A1 | 10/2008 | Roesicke et al. |
| 2008/0255440 | A1 | 10/2008 | Eilersen et al. |
| 2008/0319278 | A1 | 12/2008 | Omtveit et al. |
| 2009/0105569 | A1 | 4/2009 | Stafford |
| 2009/0259146 | A1 | 10/2009 | Freeman et al. |
| 2010/0049014 | A1 | 2/2010 | Funderburk et al. |
| 2010/0200538 | A1 | 8/2010 | Petisce et al. |
| 2010/0286714 | A1 | 11/2010 | Gym et al. |
| 2010/0324392 | A1* | 12/2010 | Yee ................ A61M 5/158 600/345 |
| 2010/0331738 | A1 | 12/2010 | Stein et al. |
| 2011/0196216 | A1 | 8/2011 | Quarder et al. |
| 2011/0288574 | A1 | 11/2011 | Curry et al. |
| 2012/0022461 | A1 | 1/2012 | Schubert et al. |
| 2012/0053608 | A1 | 3/2012 | Shoshihara et al. |
| 2012/0059231 | A1 | 3/2012 | Frey et al. |
| 2012/0083673 | A1 | 4/2012 | Al-Ali et al. |
| 2012/0116190 | A1 | 5/2012 | Iketani et al. |
| 2012/0190952 | A1 | 7/2012 | Stafford |
| 2012/0197222 | A1 | 8/2012 | Donnay et al. |
| 2012/0215083 | A1 | 8/2012 | Shoshihara et al. |
| 2012/0259192 | A1 | 10/2012 | Tsukada et al. |
| 2013/0018454 | A1 | 1/2013 | Lelkes et al. |
| 2013/0150691 | A1 | 6/2013 | Pace et al. |
| 2013/0184541 | A1 | 7/2013 | Antonio et al. |
| 2013/0267811 | A1 | 10/2013 | Pryor et al. |
| 2013/0267813 | A1 | 10/2013 | Pryor et al. |
| 2013/0313130 | A1 | 11/2013 | Little et al. |
| 2014/0031655 | A1* | 1/2014 | Stafford ............ A61B 5/6832 600/347 |
| 2014/0066730 | A1 | 3/2014 | Roesicke et al. |
| 2014/0073978 | A1 | 3/2014 | Shuros et al. |
| 2014/0121989 | A1* | 5/2014 | Kamath ............... G16Z 99/00 702/19 |
| 2015/0018643 | A1 | 1/2015 | Cole et al. |
| 2015/0080684 | A1 | 3/2015 | Frey et al. |
| 2016/0022179 | A1 | 1/2016 | Di Resta et al. |
| 2016/0058471 | A1 | 3/2016 | Peterson et al. |
| 2016/0287150 | A1 | 10/2016 | Yu |
| 2016/0331283 | A1 | 11/2016 | Rao et al. |
| 2016/0331284 | A1 | 11/2016 | Pace |
| 2017/0143243 | A1 | 5/2017 | Deck |
| 2017/0202488 | A1 | 7/2017 | Stafford |
| 2017/0202497 | A1 | 7/2017 | Yee et al. |
| 2017/0251922 | A1 | 9/2017 | Roesicke et al. |
| 2018/0325433 | A1 | 11/2018 | Prais et al. |
| 2018/0360358 | A1 | 12/2018 | Baker et al. |
| 2018/0360493 | A1* | 12/2018 | Baker ............... A61B 17/3468 |
| 2019/0151564 | A1* | 5/2019 | Schrul ................ A61M 5/326 |
| 2019/0231238 | A1* | 8/2019 | Frey ................ A61B 5/14503 |
| 2020/0178899 | A1 | 6/2020 | Chae et al. |

FOREIGN PATENT DOCUMENTS

| | | |
|---|---|---|
| CN | 101076729 A | 11/2007 |
| CN | 101596104 A | 12/2009 |
| CN | 102245236 A | 11/2011 |
| CN | 102387746 A | 3/2012 |
| CN | 102469967 A | 5/2012 |
| CN | 103156619 A | 6/2013 |
| CN | 104394757 A | 3/2015 |
| CN | 104470422 A | 3/2015 |
| CN | 204233136 U | 4/2015 |
| CN | 204233137 U | 4/2015 |
| CN | 102525413 B | 5/2015 |
| CN | 104780835 A | 7/2015 |
| CN | 105534508 A | 5/2016 |
| CN | 106535765 A | 3/2017 |
| DE | 954 712 C | 12/1956 |
| DE | 200 20 566 U1 | 1/2002 |
| DE | 20 2016 009 189 U1 | 8/2023 |
| EP | 1 475 113 A1 | 11/2004 |
| EP | 1 972 269 A1 | 9/2008 |
| EP | 2 163 190 A1 | 3/2010 |
| EP | 1 929 941 B1 | 4/2013 |
| EP | 2 348 964 B1 | 5/2013 |
| EP | 2 919 000 A1 | 9/2015 |
| EP | 2 982 303 A1 | 2/2016 |
| EP | 2 991 552 A1 | 3/2016 |
| EP | 3 202 323 A1 | 8/2017 |
| JP | 2004-049607 A | 2/2004 |
| JP | 2004-229674 A | 8/2004 |
| JP | 2008-522786 A | 7/2008 |
| JP | 2009-525794 A | 7/2009 |
| JP | 2012-071109 A | 4/2012 |
| JP | 2013-523216 A | 6/2013 |
| JP | 2014-144025 A | 8/2014 |
| JP | 2015-515305 A | 5/2015 |
| KR | 10-1393856 B1 | 5/2014 |
| KR | 10-2018-0132552 A | 12/2018 |
| RU | 133 942 U1 | 10/2013 |
| WO | WO 2006/015922 A1 | 2/2006 |
| WO | WO 2010/091005 A1 | 8/2010 |
| WO | WO 2010/091028 A1 | 8/2010 |
| WO | WO 2011/119896 A1 | 9/2011 |
| WO | WO 2011/121023 A1 | 10/2011 |
| WO | WO 2011/037030 A1 | 2/2013 |
| WO | WO 2013/090215 A2 | 6/2013 |
| WO | WO 2013/144255 A1 | 10/2013 |
| WO | WO 2014/018928 A1 | 1/2014 |
| WO | WO 2014/179343 A1 | 11/2014 |
| WO | WO 2016/012482 A1 | 1/2016 |
| WO | WO 2016/012497 A1 | 1/2016 |
| WO | WO 2016/036924 A2 | 3/2016 |
| WO | WO 2017/019224 A1 | 2/2017 |
| WO | WO 2017/037191 A1 | 3/2017 |
| WO | WO 2017/116915 A1 | 7/2017 |
| WO | WO 2017/134227 A1 | 8/2017 |

(56) References Cited

FOREIGN PATENT DOCUMENTS

| WO | WO 2018/195286 A1 | 10/2018 |
| WO | WO 2018/215421 A1 | 11/2018 |
| WO | WO 2018/222010 A1 | 12/2018 |

OTHER PUBLICATIONS

International Search Report and Written Opinion of the International Searching Authority, PCT/EP2018/086139, Mar. 4, 2019, 9 pages.

* cited by examiner

MEDICAL SYSTEM AND METHOD OF MANUFACTURING THEREOF

RELATED APPLICATIONS

This application is a continuation of U.S. patent application Ser. No. 16/898,049, filed Jun. 10, 2020, which is a continuation of International Application Serial No. PCT/EP2018/086139, filed Dec. 20, 2018, which claims priority to EP 17 209 756.0, filed Dec. 21, 2017, the entire disclosures of all of which are hereby incorporated herein by reference.

BACKGROUND

This disclosure relates to a medical system and to a method of manufacturing a medical system. The medical system specifically may be used for detecting at least one analyte in a body fluid, such as a body fluid contained in a body tissue. The medical system specifically may be used for inserting an analyte sensor contained in the system into the body tissue of the user. The medical system may be applied both in the field of home care and in the field of professional care, such as in hospitals. Other applications are feasible.

Monitoring certain body functions, more particularly, monitoring one or more concentrations of at least one analyte concentration such as at least one metabolite concentration in a body fluid, plays an important role in the prevention and treatment of various diseases. Such analytes can include by way of example, but not exclusively, blood glucose, lactate, cholesterol or other types of analytes and metabolites. Without restricting further possible applications, this disclosure will be described in the following text with reference to blood-glucose monitoring. However, additionally or alternatively, this disclosure can also be applied to other types of analytes, such as the analytes mentioned above.

For monitoring these body functions, specifically for monitoring the concentration of at least one analyte, over a period of time, specifically, electrochemical sensors are used which transcutaneously are inserted into the body tissue of the user. The sensors typically comprise an elongated flexible substrate onto which a plurality of electrodes, including one or more working electrodes and one or more further electrodes such as one or more counter electrodes and/or one or more reference electrodes are applied.

As an example, U.S. Publication No. 2010/0200538 A1 discloses methods for fabricating analyte sensor components, using IC- or MEMs-based fabrication techniques and sensors prepared therefrom. Fabrication of the analyte sensor component comprises providing an inorganic substrate having deposited thereon a release layer, a first flexible dielectric layer and a second flexible dielectric layer insulating there between electrodes, contact pads and traces connecting the electrodes and the contact pads of a plurality of sensors. Openings are provided in one of the dielectric layers over one or more of the electrodes to receive an analyte sensing membrane for the detection of an analyte of interest and for electrical connection with external electronics. The plurality of fabricated sensor components are lifted off the inorganic substrate.

As a further example, EP 2348964 B1 discloses an electrode system for measuring the concentration of an analyte under in-vivo conditions. The electrode system comprises a counter-electrode having an electrical conductor, a working electrode having an electrical conductor on which an enzyme layer containing immobilized enzyme molecules for catalytic conversion of the analyte is arranged, and a diffusion barrier that slows the diffusion of the analyte from body fluid surrounding the electrode system to enzyme molecules down. The invention provides the enzyme layer in the form of multiple fields that are arranged on the conductor of the working electrode at a distance from each other.

Several challenges in the field of continuous monitoring systems have to be addressed. One challenge resides in appropriate devices for inserting the analyte sensor into the body tissue. A further challenge resides in the fact that, in many systems, the analyte sensor has to be electrically connected to an electronics unit disposed on the surface of the skin of the user. Further challenges reside in the overall handling of the medical system which, in many cases, has to be performed by untrained users including children and elderly people, which generally requires easy handling procedures with as little steps as possible.

WO 2016/012482 A1 discloses an insertion device for inserting an analyte sensor into a body tissue, the insertion device having an insertion needle holder and a drive mechanism for linearly driving the insertion needle holder in a longitudinal direction. The drive mechanism comprises at least one actuator for actuating the drive mechanism. The actuator comprises at least one actuator arm which is pivotable about at least one axle in order to actuate the drive mechanism. The insertion device further comprises at least one protection against reuse including at least one locking mechanism. The locking mechanism is adapted to at least partially prevent a back-pivoting of the actuator arm in a direction reversing the actuation direction once the actuator arm has been pivoted by at least one threshold angle.

Similarly, WO 2016/012497 A1 discloses an insertion device for inserting an analyte sensor into a body tissue. The insertion device comprises an insertion needle holder and a drive mechanism for driving the insertion needle holder in a longitudinal direction. The drive mechanism comprises at least one actuator for actuating the drive mechanism. The drive mechanism comprises a rotor adapted to transform an actuation motion of the actuator into a motion of the insertion needle holder in the longitudinal direction. The insertion device further comprises at least one safety lock. The safety lock, in a locked position, is adapted to at least partially block a rotation of the rotor. In an unlocked position, the safety lock is adapted to permit the rotation of the rotor.

Further, disposable systems for long-term monitoring of an analyte as well as corresponding insertion devices for analyte sensors are known. WO 2017/037191 A1 discloses a kit for determining a concentration of at least one analyte in a body fluid of a user, comprising: a) a sensor module comprising i. at least one sensor element adapted to determine the concentration of the analyte, wherein the sensor element is at least partly implantable into a body tissue of the user; ii. at least one control device connected to the sensor element, wherein the control device comprises at least one data collection device adapted to collect measurement data acquired by using the sensor element, wherein the control device further comprises at least one wireless near-field communication device adapted to transmit measurement data, wherein the sensor module comprises a sensor module mechanical interface; b) at least one data reader module adapted to receive measurement data transmitted by the sensor module via wireless near-field communication, wherein the data reader module comprises at least one data storage device and is adapted to store the measurement data; c) at least one data transmission module adapted to receive measurement data transmitted by the sensor module via wireless near-field communication, wherein the data transmission module comprises at least one wireless far-field communication device, wherein the wireless far-field communication device is adapted to transmit at least part of the measurement data to an external device via wireless far-field communication. The data reader module and the data transmission module each comprise a mechanical interface adapted to reversibly engage the sensor module mechanical interface, thereby alternatively generating a fixed spatial relationship between the sensor module and the data reader module or the sensor module and the data transmission module.

Further, in EP 2 991 552 A1 systems, devices, and methods are described for changing the power state of a sensor control device in an in vivo analyte monitoring system in various manners, such as through the use of external stimuli (light, magnetics) and RF transmissions.

WO 2011/119896 A1 describes an apparatus for insertion of a medical device in the skin of a subject, as well as methods of inserting medical devices. Said apparatus includes a sheath, a device support movable between a proximal and distal position, a sharp support movable between a proximal and distal position, a handle movable between a proximal and distal position, and a driver.

U.S. Publication No. 2010/0286714 A1 describes an inserter device for inserting a medical device into the subcutaneous or intramuscular area of a patient. More specifically, an inserter device is described comprising means for providing a controlled and defined acceleration and deceleration of a penetrating member. The inserter device according to the invention comprises a housing (encompassing said penetrating member, a rotating member and driving means for rotating the rotating member around a rotating axis. The rotating member comprises transformation means transforming the rotational movement into a longitudinal movement of the penetrating member in the direction of insertion and the transformation means comprises controlling means providing a controlled variation of the velocity of the penetrating member in the direction of insertion.

U.S. Publication No. 2007/0202488 A1 describes method for determining the relative benefits of products which affect animal epithelial tissue. Also provided is a method for evaluating quantitative changes on one or more affected surfaces of epithelial tissue of a subject caused by a test product.

U.S. Publication No. 2016/0331284 A1 describes compact medical device inserters, systems incorporating the same, and related methods of use. The inserters can include a housing, a sharp support, a sharp body, and a shroud, and can apply a sensor control device to a recipient with a sensor implanted in the recipient's body. The shroud can extend from the sensor control device in a position that covers or protects the sensor and a sharp, and can be retracted by pressure placed upon the inserter against the recipient's body to cause the sharp and sensor to penetrate the body, after which the sharp can be automatically withdrawn with the aid of a biasing element.

Despite the advantages achieved by the above-mentioned devices, several technical challenges remain. Specifically, reliably connecting the analyte sensor to the electronics unit remains a challenge. Further, the trend for miniaturization generally encourages the use of disposable electronics, with a battery included. These devices, however, generally should be switched off during storage and transport and should be switched on after insertion of the analyte sensor into the body tissue. The switching, however, generally requires an additional step to be performed by the user. Further, protecting the analyte sensor and the electronics during storage, transport and use, specifically against humidity and mechanical shocks, remains to be an issue. It is therefore desirable to provide devices and methods which address the above-mentioned technical challenges.

SUMMARY

A medical system is disclosed which allows easy and user-friendly insertion of an analyte sensor into a body tissue, with few handling steps and with a high degree of protection against detrimental mechanical and environmental influences.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "protective cap," "sterility cap," and "guiding surface," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, a medical system is disclosed. The system specifically may be configured for and used for qualitatively and/or quantitatively detecting at least one analyte in a body fluid, such as one or more of the analyte listed above.

The medical system comprises:
a. a housing;
b. a preassembled functional module received in the housing, the preassembled functional module comprising
   b1. an analytical sensor for detecting at least one analyte in a body fluid of a user;
   b2. an electronics unit electrically connected to the analytical sensor; and
   b3. an insertion component for inserting the analytical sensor into a body tissue of the user; and
c. at least one removable protective cap connected to the housing, covering the preassembled functional module.

Components a., b., and c. as listed above specifically may be pre-assembled, such as to form a pre-assembled module, a pre-assembled single unit, a single factory-assembled module. This pre-assembled module or unit, specifically, may be packaged, as will be outlined in further detail below, e.g., in a blister pack.

The term "medical system" as used herein is a broad term and is to be given its ordinary and customary meaning to a person of ordinary skill in the art and is not to be limited to a special or customized meaning. The term specifically may refer, without limitation, to a system configured for performing at least one medical function. Specifically, as outlined above, the medical system may be configured for qualitatively and/or quantitatively detecting at least one analyte in a body fluid, such as in a body fluid contained in a body tissue of a user. The medical system specifically may be configured for performing at least two actions, which are the action of inserting an analytical sensor into the body tissue and to the action of detecting the analyte in the body fluid by using the analytical sensor. The medical system specifically may be, in a basic state before use, a unitary system which may be handled as one single piece. After use, which is after insertion of the analyte sensor into the body tissue, the medical system may disassemble into a disposable handling component including an inserter in a used state, and into an analyte sensor unit, with a body mount and the analyte sensor, wherein the body mount may be attached to the skin of the user and wherein the analyte sensor may protrude from the analyte sensor unit into the body tissue.

As further used herein, the term "housing" is a broad term and is to be given its ordinary and customary meaning to a person of ordinary skill in the art and is not to be limited to a special or customized meaning. The term specifically may refer, without limitation, to a basically arbitrary element which is configured for fully or partially enclosing one or more components and for providing protection for these one or more components, such as against mechanical influence and/or humidity. The housing, specifically, may be or may comprise a rigid housing, such as a rigid housing made of one or more of a plastic material, a metallic material or a cardboard material. The housing may have a front face which is configured for being disposed on the skin of the user, such as an essentially flat front face. The front face, as an example, may have a rim, with an opening enclosed by the rim, wherein the rim, as an example, is configured for tightening the skin for application of the analyte sensor. The housing, as will be explained in further detail below, may comprise, may contain or may encase one or more further components, such as an insertion actuator.

As further used herein, the term "functional module" (also referred to herein as "module") is a broad term and is to be given its ordinary and customary meaning to a person of ordinary skill in the art and is not to be limited to a special or customized meaning. The term specifically may refer, without limitation, to a module, such as a unitary module made of one or more components, specifically a plurality of interconnected components, which are configured for interacting for performing at least one function, specifically at least one medical function. In the present case, the functional module specifically may be a medical functional module configured for performing at least one medical function, such as for qualitatively and/or quantitatively detecting at least one analyte in a body fluid.

As further used herein, the term "preassembled" generally refers to the fact that an assembly process has already taken place. Thus, a "preassembled" medical system comprises the functional module as defined above in a preassembled state, which means the components of the functional module already being assembled, such as by being mechanically and/or electrically interconnected, thereby being ready for use for the at least one function, such as the at least one medical function, e.g., for the at least one analytical function. The pre-assembling specifically may take place in a factory, thereby rendering the preassembled functional module a factory-assembled functional module. Specifically, the medical system may be configured such that the at least one preassembled functional module is fully covered by the combination of the housing and the protective cap, such that the user may not see or manipulate the preassembled functional module without opening the medical device, e.g., without removing the protective cap.

As further used herein, the term "received in the housing" generally refers to the fact that the preassembled functional module is fully or partially surrounded by the housing. As outlined above, specifically, the housing may comprise at least one receptacle for receiving the preassembled functional module. The receptacle, as an example, may be located in a front face of the housing, wherein the receptacle may fully or partially be surrounded by a frame formed, e.g., by the housing. The receptacle may be covered by the protective cap, such that, when the protective cap is removed from the housing, the functional module is accessible and may be placed on the skin of the user.

The term "sensor" as used herein is a broad term and is to be given its ordinary and customary meaning to a person of ordinary skill in the art and is not to be limited to a special or customized meaning. The term specifically may refer, without limitation, to an arbitrary element or device configured for detecting at least one condition or for measuring at least one measurement variable. The sensor specifically may be or may comprise an analyte sensor for at least partial implantation into a body tissue of a user, more specifically an analyte sensor for continuous monitoring of the analyte. The sensor specifically may be a monolithic sensor element.

Consequently and as further used herein, the term "analytical sensor" is a broad term and is to be given its ordinary and customary meaning to a person of ordinary skill in the art and is not to be limited to a special or customized meaning. The term specifically may refer, without limitation, to a sensor according to the definition given above, which is configured for being used for analytical purposes. Specifically, the analytical sensor may be configured for qualitatively and/or quantitatively detecting at least one analyte in a body fluid of the user, such as one or more of the analytes listed above, more specifically glucose. The body fluid, as an example, may be or may contain one or more of blood or interstitial fluid. The analytical sensor specifically may be configured for long-term monitoring of the analyte. The analytical sensor, as an example, may be configured for being placed into the body tissue and for remaining therein for at least one week, by providing measurement data over this period of use. The analytical sensor specifically may be or may comprise an electrochemical analytical sensor, as will be described in further detail below.

The term "electronics unit" (also referred to as "electronics" or "electronics assembly") as used herein is a broad term and is to be given its ordinary and customary meaning to a person of ordinary skill in the art and is not to be limited to a special or customized meaning. The term specifically may refer, without limitation, to a unit, such as a unit which may be handled as a single piece, which is configured for performing at least one electronic function. Specifically, the electronics unit may have at least one interface for being connected to the analytical sensor, wherein the electronics unit may provide at least one electronic function interacting with the analytical sensor, such as at least one measurement function. As will be outlined in further detail below, the electronics unit specifically may be configured for measuring at least one voltage and/or for measuring at least one current, thereby interacting with the analytical sensor, specifically the electrochemical analytical sensor. The electronics unit specifically may comprise at least one electronics unit housing, wherein the analytical sensor, e.g., with a proximal end, may protrude into the housing and may be electrically connected with at least one electronic component within the housing. As an example, the proximal end and/or at least one contact portion of the electrochemical sensor may protrude into the housing and, therein, may be electrically connected to at least one electronic component, such as to at least one printed circuit board and/or at least one contact portion of the electronics unit, e.g., by one or more of a soldering connection, a bonding connection, a plug, a clamping connection or the like. The electronics unit, as will be outlined in further detail below, specifically may be used as a transmitter for transmitting measurement data to at least one external device, such as to at least one receiver, e.g., wirelessly.

The electronics unit is electrically connected to the analytical sensor. Thus, an electrical connection exists between the analytical sensor and the electronics unit. Via this electrical connection, the electronics unit may interact with the analytical sensor for performing at least one electrochemical measurement. The electrical connection specifically, as outlined above, may be established by at least one connection portion of the analytical sensor protruding into a housing of the electronics unit. The functional module may be preassembled in the sense that, the electronics unit is already electrically connected to the analytical sensor when the functional module is received in the housing, with the protective cap being connected to the housing. Specifically, the electronics unit may be irreversibly electrically connected to the analytical sensor. Thus, specifically, no need for assembly of the electronics unit and the analytical sensor is given, since, in the preassembled functional module, the electronics unit and the analytical sensor are already connected, electrically and optionally also mechanically.

The term "insertion component" (also referred to herein as an "inserter") as used herein is a broad term and is to be given its ordinary and customary meaning to a person of ordinary skill in the art and is not to be limited to a special or customized meaning. The term specifically may refer, without limitation, to an element or a combination of elements which are configured for inserting at least one component into a body tissue of a user, e.g., transcutaneously or subcutaneously. Thus, specifically, the at least one insertion component may be or may comprise at least one insertion cannula, with a tip or sharp configured for piercing the skin of the user and further, optionally, with at least one slot configured for receiving at least a part of the analytical sensor. The insertion component may comprise further elements, such as at least one holder for manipulating or holding the insertion component such as the insertion cannula.

The electronics unit specifically may have an opening there through, through which the insertion component may protrude. Thus, as an example, the electronics unit may have an upper side and a lower side, with the lower side facing towards the skin of the user and with the upper side facing towards the housing, such as towards an insertion actuator. The insertion actuator may drive the insertion component, such as the insertion cannula, through the opening, such as through a through hole in in a housing of the electronics unit.

The term "protective cap" as used herein is a broad term and is to be given its ordinary and customary meaning to a person of ordinary skill in the art and is not to be limited to a special or customized meaning. The term specifically may refer, without limitation, to an element configured for partially covering at least one other device, component or element, thereby providing at least partial protection against mechanical and/or environmental influences. The protective cap specifically may be fully or partially made of at least one rigid material, such as of at least one plastic material and/or at least one metal. The protective cap specifically may have an opening which is configured to be directed towards the housing of the medical system. The protective cap specifically may be made essentially rotationally symmetric, e.g., by having an axial rotational symmetry about an axis such as a cylinder axis. The protective cap, as an example, may be designed as a cylinder, a hemisphere or as a dome.

The protective cap, as an example, may be connected to the housing by at least one of a form-fit or a force-fit connection. Specifically, a rim of the protective cap may be pushed over a rim of the housing or vice versa. Thus, as an example, the protective cap may have a circular, oval or polygonal rim which fits tightly over the rim of the housing having a corresponding shape, or vice versa. There may be an overlap region in the connected state, in which the protective cap overlaps with the housing or vice versa.

As outlined above, the housing specifically may comprise at least one receptacle for receiving the electronics unit, the receptacle being open towards an end of the housing covered by the protective cap. Therein, as an example, the receptacle may comprise at least one open space, being open towards the front face of the housing, wherein the electronics unit is received within the open space. The electronics unit may be held in the receptacle by at least one holding means, such as by at least one hook or the like, which may free the electronics unit once applied to the skin of the user, e.g., after insertion of the analytical sensor into the body tissue.

As outlined above, the electronics unit specifically may comprise at least one electronics component. Specifically, the electronics unit may comprise at least one of: a measurement device for providing electrochemical measurement values, specifically at least one of an amperometric or a potentiostatic measurement device; a transmitter for transmitting measurement values to at least one external receiver; an integrated data storage device; an integrated battery. These electronic components generally are known in the art of long-term monitoring one or more analytes, such as in from one or more of the above-mentioned prior art documents.

As outlined above, specifically in an assembled state of the analytical system and prior to removal of the protective cap, the analytical sensor is fixedly electrically connected to the electronics unit. Thus, as opposed to systems in which the analytical sensor is connected to an electronics unit during insertion, in the present case, the analytical sensor specifically may be electrically connected to electronics unit prior to insertion. Thus, the analytical sensor and the electronics unit may form part of a disposable unit.

The analytical sensor specifically may be an electrochemical analytical sensor. Thus, the electrochemical analytical sensor specifically may have at least one working electrode and at least one further electrode selected from the group consisting of a counter electrode and a reference electrode. As an example, the at least one working electrode may comprise at least one chemical reagent for detecting the at least one analyte, such as at least one chemical reagent containing at least one enzyme. The at least one working electrode and the at least one further electrode specifically may be connected to the electronics unit via at least two electrical leads.

The preassembled functional module may further comprise at least one sterility cap at least partially surrounding the insertion component.

The term "sterility cap" as used herein is a broad term and is to be given its ordinary and customary meaning to a person of ordinary skill in the art and is not to be limited to a special or customized meaning. The term specifically may refer, without limitation, to an element such as a cover which is configured for maintaining a sterile atmosphere in a space fully or partially surrounded by the element. The sterility cap, as an example, may be a rigid sterility cap, e.g., made of a rigid plastic material and/or a metal. The sterility cap, as an example, may have a rotational symmetry about an axis which, as an example, may be identical to a rotational symmetry axis of the protective cap and/or of a rotational symmetry axis of the housing. The sterility cap, as an example, may have an elongated shape, with a length exceeding its diameter or equivalent diameter by at least a factor of 2, more preferably by at least a factor of five. The sterility cap, as an example, may have a length of 5 to 20 mm, e.g., a length of 10 to 15 mm.

As outlined above, the insertion component specifically may comprise at least one insertion cannula. The insertion cannula may fully or partially be received in the sterility cap. The sterility cap, as an example, may have an elongated shape, with a closed end and an open end, with the insertion cannula protruding from the open end into the sterility cap, with the tip of the insertion cannula facing the closed end. The analytical sensor may partially be received in the insertion cannula, such as in a slot of the insertion cannula. The insertion component may further comprise at least one holder for the insertion cannula, wherein the holder, the insertion cannula and the sterility cap form components of a sterile container for the analytical sensor. The holder, as an example, may comprise a rigid component connected to a proximal end of the insertion cannula, i.e., to an end of the insertion cannula opposing the tip of the insertion cannula. The insertion cannula, as an example, may be connected to the holder by gluing and/or by injection molding and/or, e.g., by other means of material engagement. The holder, as an example, may have a cylindrical shape.

The protective cap specifically may be removable from the housing by pulling off the protective cap from the housing. Thus, as outlined above, the protective cap may, in a stage connected to the housing, overlap with the housing or vice versa. The protective cap specifically may be stuck onto the housing in a tight fashion. The housing specifically may comprise at least one guiding surface for guiding the protective cap during pulling off the protective cap, specifically a circumferential guiding surface. Thus, the guiding surface may be an outer surface of the housing, such as an outer surface having one of a circular cross-section, and oval cross-section or a polygonal cross-section. In the connected state, the protective cap may overlap with the housing within the guiding surface. When being pulled off from the housing, the protective cap, such as an inner surface of the protective cap, may slide over the guiding surface.

The sterility cap specifically may be fixedly connected to the protective cap. Thus, the sterility cap may be configured for being pulled off from the insertion component when the protective cap is pulled off from the housing. Still, the sterility cap may be distinct from the protective cap. Thus, even though the sterility cap may be received within the protective cap, the wall of the sterility cap should be different from the wall of the protective cap. The sterility cap, however, may be connected to the protective cap at a distal end of the sterility cap, e.g., by one or more of a form-fit connection, a force-fit connection or a connection by material engagement such as a gluing or a connection by injection molding. The protective cap and the sterility cap specifically may be made of different materials.

The option of connecting the action of removing the protective cap from the housing with the action of pulling off the sterility cap from the insertion component provides a plurality of further options and advantages. Thus, as an example, the preassembled functional module may comprise at least one guiding surface for guiding the sterility cap during pulling off the sterility cap from the insertion component. A length of the guiding surface of the housing may exceed a length of the guiding surface for the sterility cap, specifically by at least a factor of 2, more specifically by at least a factor of 5 or by at least a factor of 10. Additionally or alternatively, a length of the guiding surface of the housing may exceed a length of the sterility cap, specifically such that the sterility cap is fully pulled off from the insertion component before the guiding by the guiding surface of the housing ends when the protective cap is pulled off from the housing. Thus, in other words, by coupling the action of removing the protective cap from the housing, e.g., by pulling off the protective cap from the housing, with the action of removing the sterility cap from the insertion component, e.g., from the insertion cannula, provides the option of guiding the sterility cap via guiding the protective cap by the housing, such that the sterility cap performs a well-defined movement until the insertion component, e.g., the insertion cannula, is fully free and until the sterility cap is fully removed from the insertion component. Thus, the risk of mechanically damaging the insertion component, e.g., the insertion cannula, during removal of the sterility cap may be significantly reduced, since the movement of the sterility cap is well-defined and may be directed precisely along a longitudinal axis of the insertion component, e.g., the insertion cannula, specifically over the full length of the insertion cannula.

The guiding surface of the housing specifically may provide for at least one movement selected from the group consisting of: a translational movement of the protective cap and the sterility cap when the protective cap is pulled off from the housing; a rotational movement of the protective cap and the sterility cap when the protective cap is pulled off from the housing; both a translational and a rotational movement of the protective cap and the sterility cap when the protective cap is pulled off from the housing. Thus, several movements are possible and may even be combined. As an example, when pulling off the protective cap, the protective cap may only perform a translational movement, e.g., along a longitudinal axis of the medical system. However, rotational movements may be introduced additionally or alternatively. As an example, the at least one guiding surface may provide for one or more spiral-shaped guiding elements or guiding surfaces, thereby introducing a rotational movement. The rotational movement specifically may also be used for blocking or unlocking actions. Thus, as an example, the guiding surface of the housing may provide at least a rotational component when the protective cap is pulled off from the housing. The sterility cap may be connected to the preassembled functional module by at least one bayonet connection, wherein, by the rotational component, the bayonet connection may be untightened and the sterility cap may be removable from the preassembled functional module.

The medical system may further comprise at least one indicator seal connected to the protective cap and the housing. As used herein, the term "indicator seal" specifically may refer to an element which is visible to a user and which indicates whether the medical system has been used before, specifically whether the protective cap has already been removed from the housing before. Thus, the indicator seal may also be referred to as an originality seal. The medical system may comprise one or more tamper-evident closure means and the indicator seal may be part of the tamper-evident closure means. The indicator seal, as an example, may be configured to be broken when the protective cap is removed from the housing. The indicator seal specifically may comprise one of a sealing foil and a sealing tape. The indicator seal may exemplarily be an originality closure.

The indicator seal may provide further functionality to the medical system. Thus, the indicator seal may also provide sealing properties, such as against ingression of humidity into the housing and/or into the protective cap. Additionally or alternatively, the indicator seal may be light-tight. This option is specifically useful in connection with the option of the electronics unit being activated by an optical switch, which will be explained in further detail below.

Thus, generally, the medical system may be configured such that the electronics unit is switched on when the protective cap is removed from the housing. The electronics unit specifically may be switched on by at least one switching mechanism selected from the group consisting of: a mechanical switch connected to the cap, wherein the mechanical switch is switched on when the protective cap is removed from the housing; a light-sensitive switch, wherein the light-sensitive switch is switched on by ambient light when the protective cap is removed from the housing; a liner covering a battery of the electronics unit, wherein the liner is pulled off when the protective cap is removed from the housing. Thus, as an example, the protective cap may comprise a pin or a ribbon which is connected to the electronics unit. By removing the protective cap, e.g., by pulling off the protective cap, the pin or the ribbon may set free a switch within the electronics unit, thereby switching on the electronics unit. Additionally or alternatively, the electronics unit may comprise a photodiode, a phototransistor or another light-sensitive element which is configured for detecting the removal of the protective cap and ambient light shining on to the electronics unit, the electronics unit being configured for being switched on by the detection of the light. Additionally or alternatively, the light-sensitive element may generate a photocurrent or a photovoltage sufficient for switching on the electronics unit.

The medical system may further comprise at least one adhesive plaster for attaching the electronics unit to a skin surface of a user. The adhesive plaster may be attached directly or indirectly to the electronics unit or to a part which, e.g., during insertion of the analytical sensor, is connected to the electronics unit. The adhesive plaster may be or may comprise an adhesive surface, e.g., an adhesive surface of a rigid part or of a flexible bandage. The adhesive plaster, in an initial state of the medical system with the protective cap being connected to the housing, may be covered by at least one removable liner. The liner may be connected to the protective cap, e.g., directly by attaching the liner or a part thereof such as a ribbon or a latch of the liner to the protective cap, or indirectly, e.g., by connecting the protective cap and the liner by using a ribbon, a protrusion of the protective cap or the like. By these means or other means, the liner thus may be configured for being pulled off from the adhesive plaster when the protective cap is removed from the housing.

The medical system may further comprise at least one insertion actuator. The term "insertion actuator" as used herein is a broad term and is to be given its ordinary and customary meaning to a person of ordinary skill in the art and is not to be limited to a special or customized meaning. The term specifically may refer, without limitation, to an arbitrary device which is configured for directly or indirectly inserting at least one insertable element into a body tissue. The insertion actuator may comprise at least one mechanical device which is configured for driving forward the insertable element or the insertion component such as the insertion cannula into the body tissue. The insertion actuator, as an example, may comprise at least one slider connected to the insertion component or the holder for the insertion component and configured for performing a forward linear motion in an insertion direction and, optionally, a backward linear motion in an opposite direction. As an example, the slider may be driven by at least one spring element, which may be pre-tensioned or biased in the forward direction or in the backward direction. Additionally or alternatively, the slider may be connected to at least one actuation button which may be pushed by the user, thereby driving the slider in the forward direction. The insertion actuator, thus, may be configured for driving the insertion component into the body tissue and, optionally, backwards again after insertion of the insertable analytical sensor. The backward motion, as an example, for retracting the insertion component such as the insertion cannula from the body tissue, may be driven by a return spring or by a motion inverter. The insertion actuation by the insertion actuator may further initiate or provide other actions, such as an assembly of components of the body mount, such as components providing a shell for the electronics unit, and/or an attachment of a body mount to the skin of the user. Inserting actuators configured for driving an insertion motion as known to the skilled person may also be used in the context of this disclosure. As an example, reference may be made to the actuators disclosed in the above-mentioned documents WO 2016/012482 A1, WO 2016/012497 A1 or WO 2017/037191 A1 and the prior art cited therein. These insertion actuators may also be used in the context of this disclosure, directly or with context-specific modifications. Generally, the insertion actuator may be configured for advancing the insertion component after removal of the protective cap from the housing and for inserting the analytical sensor into the body tissue.

As indicated above, the medical system may comprise a body mount. The term "body mount" as used herein is a broad term and is to be given its ordinary and customary meaning to a person of ordinary skill in the art and is not to be limited to a special or customized meaning. The term specifically may refer, without limitation, to an analytical component interacting with the analytical sensor configured for being mounted to the skin of the user. The body mount may comprise the adhesive plaster and a cradle attached to the adhesive plaster and configured for receiving the electronics unit, as well as, fully or partially, the electronics unit. Further, optionally, the body mount may comprise an upper shell covering the electronics unit, wherein, as an example, the upper shell may be connected to the cradle, thereby forming a shell fully or partially enclosing the electronics unit. The analytical sensor, in an inserted state with the body mount attached to the skin, may protrude from a lower side of the electronics unit, through an opening in the cradle and an opening in the adhesive plaster, into the body tissue.

In an initial state, before removing the protective cap from the housing, the body mount may be received in the housing. Therein, the body mount may be received in the housing in an assembled state or in a disassembled state, wherein, in the latter case, an assembly may take place during insertion or after insertion of the analytical sensor into the body tissue. Thus, generally, the body mount may comprise at least one cradle for attachment to the skin of the user and at least one upper shell, wherein the electronics unit is received in the upper shell. The cradle and the upper shell may be disassembled before actuation of the insertion actuator. The medical system, specifically the cradle and the upper shell, may be configured for being assembled when the insertion actuator is actuated. Thus, as an example, when the insertion actuator moves forward towards the skin of the user, the adhesive plaster and/or the cradle may reach the skin and, thereby, a forward movement of these components may be stopped, wherein the electronics unit with the analytical sensor connected thereto and, optionally, the upper shell still may move forward towards the skin. Thereby, firstly, the electronics unit may be inserted into the cradle. Secondly, afterwards, the upper shell may be put on top and may be locked to the electronics unit and/or to the cradle, thereby forming a casing or shell for the electronics unit. Simultaneously, during the forward motion, the insertion component may be driven into the body tissue, thereby inserting the analytical sensor into the body tissue. Afterwards, the insertion component may be retracted from the body tissue, with the analytical sensor remaining in the body tissue.

As outlined above, the insertion actuator specifically may comprise at least one pushbutton. The pushbutton, as an example, may comprise a linearly slidable pushbutton which may be pushed in a linear direction, such as perpendicular to the skin of the user. The insertion actuator, specifically the pushbutton, may be comprised in the housing, may be attached to the housing or may be integrated into the housing. As further outlined above, the insertion actuator further may be configured for retracting the insertion component from the body tissue after insertion of the analytical sensor.

The protective cap, in addition or as an alternative to one or more of the above-mentioned functions, may provide further functionality. Thus, as an example, the protective cap may also provide functions for keeping the level of humidity within the closed medical system, before removal of the protective cap, low. Thus, specifically, the protective cap may comprise a plurality of chambers at least partially filled with a desiccant such as silica gel. As an example, on one or more inner surfaces facing towards the housing, the protective cap may comprise one or more separating walls protruding from the at least one in the surface into an interior of the protective cap, thereby forming the chambers, which, as an example, may be open towards the housing. The chambers may fully or partially be filled with the at least one desiccant.

As a further, additional or alternative measure for protecting the analytical sensor and/or the electronics unit in the medical system from humidity, the medical system may further comprise at least one humidity seal received in between the protective cap and the housing. Thus, as outlined above, the protective cap may overlap with the housing in an overlap region, which may also provide the at least one guiding surface. Within this overlap region, at least one humidity seal may be provided, such as by providing O-ring and/or by providing a line of glue, such as a circumferential line. The humidity seal may be broken when the protective cap is removed from the housing.

The medical system may further comprise at least one package. The package specifically may be an airtight and/or a humidity-tight package such as a blister pack. The remaining components of the medical system may be enclosed in the closed package, specifically in the blister pack. Thus, the housing, the preassembled functional module and the removable protective cap connected to the housing may form a single, closed unit of the medical system which may be enclosed in the closed package, with the preassembled functional module, e.g., preassembled by factory assembly, enclosed in the housing with the protective cap attached thereto. Thus, once the user opens the closed package, taking out the unit, the unit may be ready to use.

In a further aspect of this disclosure, a method of manufacturing a medical system, specifically of a medical system as disclosed above or as disclosed in further detail below, is proposed. The method comprises the steps disclosed in the following. The steps specifically may be performed in the given order. Still, a different order is possible. The method may comprise additional steps which are not mentioned. It is further possible to perform one or more of the method steps repeatedly. Further, two or more of the method steps may be performed in a timely overlapping fashion or simultaneously.

The method steps comprised by the method of manufacturing the medical system are:
  i. providing a housing;
  ii. preassembling a functional module, the preassembled functional module comprising:
    an analytical sensor for detecting at least one analyte in a body fluid of a user;
    an electronics unit electrically connected to the analytical sensor; and
    an insertion component for inserting the analytical sensor into the body tissue;
  iii. receiving the preassembled functional module in the housing; and
  iv. connecting at least one removable protective cap to the housing, thereby covering the preassembled functional module.

As indicated above, the method specifically may be used for manufacturing the medical system as proposed therein, such as according to any one of the embodiments disclosed above and/or according to any one of the embodiments disclosed in further detail below.

Further proposed is a method of using the medical system according to this disclosure, such as the medical system according to any one of the embodiments disclosed above or according to any one of the embodiments disclosed in further detail below. The method may comprise the following steps, preferably in the given order. A different order, however, may also be feasible. Further, again, one, more than one or even all of the method steps may be performed repeatedly. Further, two or more of the method steps may also be performed fully or partially simultaneously. The method may comprise further steps.

The method comprises:
I. providing the medical system,
II. removing the protective cap from the housing,
III. placing the housing against the skin of the user, and
IV. inserting the analytical sensor into the body tissue of the user.

Method step I. may also include removing a unit of the medical system, comprising the housing, the protective cap and the preassembled functional module, from a closed package, such as from a blister pack.

Method step II. may comprise a plurality of sub-steps, which may be initiated by removing the protective cap from the housing. One or more of the sub-steps disclosed in the following may be comprised. Thus, as indicated above, the steps may comprise switching on the electronics unit. Additionally or alternatively, the step may comprise removing a sterility cap from the insertion component. Additionally or alternatively, the step may also comprise breaking an indicator seal. Additionally or alternatively, the step may also comprise removing a liner from an adhesive plaster.

Method step III. may comprise attaching an adhesive plaster to the skin and, further, optionally, placing a cradle onto the skin and adhering the cradle to the skin with the adhesive plaster.

Similarly, method step IV. may comprise one or more of the following sub-steps. Thus, as an example, the method step may comprise the step of initiating the insertion by activating an insertion actuator, such as by pushing a push-button. The step may also comprise an assembly of a body mount, e.g., by assembling the adhesive plaster, the cradle and the electronics unit as well as, optionally, an upper shell to form a single unit.

The medical system and the method according to this disclosure provide a large number of advantages over known methods and devices. Thus, specifically, the above-mentioned technical challenges of known inserting devices, specifically for continuous monitoring sensors, are addressed.

Specifically, the medical system may provide for a fully disposable continuous monitoring system, such as a fully disposable continuous glucose monitoring system. The functional module may be preassembled, such that the body mount, the electronics unit and the analytical sensor are already in an assembled state. The functional module in combination with the housing and the removable protective cap may also form a preassembled module and may be delivered to the customer in such a preassembled fashion. Thus, no further assembling steps generally needs to be performed by the user. The preassembled module may comprise the housing, the functional module and the protective cap. The protective cap may combine different functionalities in one element. Such functionalities may include one or more of ensuring a sterile and safe environment, providing a simple user handling for removal of the protective cap, providing for a sterile barrier of the analytical sensor compartment, initializing of medical system, providing for tamper-evident closure means such as the indicator seal or further functionalities. The protective cap specifically may ensure, in a simple and cost efficient fashion, a high robustness, and easy system initialization, as well as easy handling steps, in one system element. The medical system may provide for a sensor system for monitoring an analyte concentration, comprising an assembly of the analytical sensor, an inserter and an electronics unit. The analytical sensor, the inserter and the electronics unit may be preassembled prior to application of the analytical sensor. This pre-assembly specifically may be a factory pre-assembly, prior to unpacking the system by a user. The assembly may further comprise the protective cap which may fix the inserter, the analytical sensor and the electronics unit in place and, upon removal of the protective cap, may allow for insertion of the analytical sensor into subcutaneous tissue. as outlined above, the protective cap may be part of an initialization concept for the medical system, e.g., by the electronics unit comprising at least one photosensitive element which detects ambient light once the protective cap is removed, thereby initiating the electronics unit in connection with the analytical sensor. Additionally or alternatively, the protective cap may incorporate guiding means for simpler user handling on removal of the protective cap, e.g., via a screw that also may be used as seal. Additionally or alternatively, the protective cap may include a tamper-evident closure, which may also aid as a barrier for liquid or humidity.

Thus, the protective cap specifically may provide multiple functions and multiple solutions for the technical challenges. Thus, as indicated above, by providing a protection against humidity, the protective cap may protect sensitive components of the analytical sensor, such as the substrate, enzymes or the like. Thereby, the storage lifetime may be increased. No additional desiccant in an outer packaging, including the requirement for additional space, is generally required. The desiccant may be placed in the protective cap, e.g., by placing the desiccant directly into the protective cap and/or by implementing one or more packages of desiccant into the protective cap, e.g., by material engagement such as gluing and/or by formfitting connection. The amount of desiccant may be adapted to the desired storage lifetime of the medical system.

The protective cap may further, as indicated above, be used as a switch for switching on the electrical unit, such as the transmitter. Thus, as outlined above, several functionalities and/or switching concepts may be implemented. As an example, optical switches such as one or more phototransistors may be used, wherein, when removing the protective cap from the housing, ambient light may switch on the electronics unit. The protective cap generally may be designed by using a light-tight material, in order to avoid unintentionally switching on the electronics unit and in order to provide a light barrier which is broken immediately before use of the medical system by the user. An appropriate geometry of the protective cap may be chosen.

The protective cap may further provide mechanical protection. Thus, an additional mechanical protection for the entire medical system is provided. Thus, by appropriate and/or flexible design of the protective cap or of parts thereof, the protective cap alone or in conjunction with the housing may absorb or reduce mechanical influences and shocks. Thus, as an example, without the protective cap, the medical system may be dropped onto a sterility cap covering the insertion component such as the insertion cannula and thereby inducing damages to the insertion component. Without the protective cap, other constructive protective measures would be required.

Further, as outlined above, the sterility cap and the removal of the same impose further technical challenges onto typical medical systems. Due to the length of the insertion component, such as the length of the insertion cannula, pulling off the sterility cap typically requires a minimum length of guiding, such as a minimum length of 10 mm, in order to safely remove the sterility cap from the insertion component and in order to avoid damaging of the insertion component by the sterility cap during removal. By connecting the sterility cap to the protective cap, the guiding of the sterility cap during removal may be increased and improved. Thus, as an example, the protective cap may be guided by the housing when removing the protective cap from the housing, wherein a guiding length or guiding distance increases the length of the insertion component and/or the length of the protective cap. Thus, by this increased guiding, as an example, transversal movements may be possible only after the sterility cap has safely cleared the insertion component such as the cannula.

The protective cap may further be used for preparing the body mount for attachment to the skin of the user. Thus, as outlined above, the removal of the protective cap from the housing may also be used for removing a liner from an adhesive plaster.

The protective cap may further be used in connection with an indicator seal, such as the originality closure, and/or with a humidity barrier. Thus, in between the protective cap and the housing, the indicator seal may be provided, such as by providing a visible adhesive tape which clearly indicates whether the medical system has been opened and/or damaged. The indicator seal may also provide an additional barrier against humidity and, thus, may render an additional package obsolete. Additionally or alternatively, a humidity barrier may be provided in between the protective cap and the housing or the pushbutton of the actuator.

Further, as outlined above, when removing the protective cap from the housing, various movements are feasible. Thus, purely translational movements as well as combinations with rotational movements are feasible. Further, the movement of the protective cap may be translated into an appropriate movement of the sterility cap. Thus, even if the protective cap performs a purely translational movement, this translational movement may be translated into a rotational component of the sterility cap or vice versa. For transforming a movement of the protective cap into a desired movement of the sterility cap, the sterility cap may be connected to the protective cap via one or more guiding elements, such as one or more cam controls. Thereby, the sterility cap may be unlocked from one or more of the insertion component, the electronics unit, the holder or the preassembled functional module, e.g., by a bayonet lock. Generally, by making use of one or more of these options, the geometry of the medical system, such as the geometry of the insertion actuator, may be separated from the geometry of other components of the medical system and, generally, may be chosen freely. The insertion actuator not necessarily has to have a round cross-section, and the electronics unit may be optimized onto a small area. Generally, the geometry may be chosen independent from the functions of the components, such as of the transmitter.

Summarizing and without excluding further possible embodiments, the following embodiments may be envisaged:

Embodiment 1: A medical system, comprising:
a. a housing;
b. a preassembled functional module received in the housing, the preassembled functional module comprising:
b1. an analytical sensor for detecting at least one analyte in a body fluid of a user;
b2. an electronics unit electrically connected to the analytical sensor; and
b3. an insertion component for inserting the analytical sensor into a body tissue of the user; and
c. at least one removable protective cap connected to the housing, covering the preassembled functional module.

Embodiment 2: The medical system according to the preceding embodiment, wherein the housing comprises at least one receptacle for receiving the electronics unit, the receptacle being open towards an end of the housing covered by the protective cap.

Embodiment 3: The medical system according to any one of the preceding embodiments, wherein the electronics unit comprises at least one of: a measurement device for providing electrochemical measurement values, specifically at least one of an amperometric or a potentiostatic measurement device; a transmitter for transmitting measurement values to at least one external receiver; an integrated data storage device; an integrated battery.

Embodiment 4: The medical system according to any one of the preceding embodiments, wherein the analytical sensor is fixedly electrically connected to the analytical sensor.

Embodiment 5: The medical system according to any one of the preceding embodiments, wherein the analytical sensor is an electrochemical analytical sensor, having at least one working electrode and at least one further electrode selected from the group consisting of a counter electrode and a reference electrode, wherein the at least one working electrode and the at least one further electrode are connected to the electronics unit via at least two electrical leads.

Embodiment 6: The medical system according to any one of the preceding embodiments, wherein the preassembled functional module further comprises at least one sterility cap at least partially surrounding the insertion component.

Embodiment 7: The medical system according to the preceding embodiment, wherein the insertion component comprises at least one insertion cannula, with the analytical sensor partially received therein.

Embodiment 8: The medical system according to the preceding embodiment, wherein the insertion component further comprises at least one holder for the insertion cannula, wherein the holder, the insertion cannula and the sterility cap form components of a sterile container for the analytical sensor.

Embodiment 9: The medical system according to any one of the three preceding embodiments, wherein the protective cap is removable from the housing by pulling off the protective cap from the housing, wherein the housing comprises at least one guiding surface for guiding the protective cap during pulling off the protective cap, specifically a circumferential guiding surface.

Embodiment 10: The medical system according to the preceding embodiment, wherein the sterility cap is connected to the protective cap, wherein the sterility cap is configured for being pulled off from the insertion component when the protective cap is pulled off from the housing.

Embodiment 11: The medical system according to the preceding embodiment, wherein the preassembled functional module comprises at least one guiding surface for guiding the sterility cap during pulling off the sterility cap from the insertion component.

Embodiment 12: The medical system according to the preceding embodiment, wherein a length of the guiding surface of the housing exceeds a length of the guiding surface for the sterility cap, specifically by at least a factor of 2, more specifically by at least a factor of 5 or by at least a factor of 10.

Embodiment 13: The medical system according to any one of the three preceding embodiments, wherein a length of the guiding surface of the housing exceeds a length of the sterility cap, specifically such that the sterility cap is fully pulled off from the insertion component before the guiding by the guiding surface of the housing ends when the protective cap is pulled off from the housing.

Embodiment 14: The medical system according to any one of the four preceding embodiments, wherein the guiding surface of the housing provides at least one movement selected from the group consisting of: a translational movement of the protective cap and the sterility cap when the protective cap is pulled off from the housing; a rotational movement of the protective cap and the sterility cap when the protective cap is pulled off from the housing; both a translational and a rotational movement of the protective cap and the sterility cap when the protective cap is pulled off from the housing.

Embodiment 15: The medical system according to the preceding embodiment, wherein the guiding surface of the housing provides at least a rotational component when the protective cap is pulled off from the housing, wherein the sterility cap is connected to the preassembled functional module by at least one bayonet connection, wherein, by the rotational component, the bayonet connection is untightened and the sterility cap is removable from the preassembled functional module.

Embodiment 16: The medical system according to any one of the preceding embodiments, further comprising at least one indicator seal connected to the protective cap and the housing, wherein the indicator seal is configured to be broken when the protective cap is removed from the housing.

Embodiment 17: The medical system according to the preceding embodiment, wherein the indicator seal comprises one of a sealing foil and a sealing tape.

Embodiment 18: The medical system according to any one of the two preceding embodiments, wherein the indicator seal is light-tight.

Embodiment 19: The medical system according to any one of the preceding embodiments, wherein the medical system is configured such that the electronics unit is switched on when the protective cap is removed from the housing.

Embodiment 20: The medical system according to the preceding embodiment, wherein the electronics unit is switched on by at least one switching mechanism selected from the group consisting of: a mechanical switch connected to the cap, wherein the mechanical switch is switched on when the protective cap is removed from the housing; a light-sensitive switch, wherein the light-sensitive switch is switched on by ambient light when the protective cap is removed from the housing; a liner covering a battery of the electronics unit, wherein the liner is pulled off when the protective cap is removed from the housing.

Embodiment 21: The medical system according to any one of the preceding embodiments, wherein the medical system further comprises at least one adhesive plaster for attaching the electronics unit to a skin surface of a user, wherein the adhesive plaster is covered by a liner, wherein the liner is connected to the protective cap, wherein the liner is configured for being pulled off from the adhesive plaster when the protective cap is removed from the housing.

Embodiment 22: The medical system according to any one of the preceding embodiments, wherein the medical system further comprises at least one insertion actuator, wherein the insertion actuator is configured for advancing the insertion component after removal of the protective cap from the housing and for inserting the analytical sensor into the body tissue.

Embodiment 23: The medical system according to the preceding embodiment, wherein the medical system further comprises a body mount received in the housing, wherein the electronics unit is at least partially comprised in the body mount.

Embodiment 24: The medical system according to the preceding embodiment, wherein the body mount comprises at least one cradle for attachment to the skin of the user and at least one upper shell, wherein the electronics unit is received in the upper shell, wherein the cradle and the upper shell are disassembled before actuation of the insertion actuator and wherein the cradle and the upper shell are configured for being assembled when the insertion actuator is actuated.

Embodiment 25: The medical system according to any one of the three preceding embodiments, wherein the insertion actuator comprises at least one pushbutton.

Embodiment 26: The medical system according to any one of the four preceding embodiments, wherein the insertion actuator is configured for retracting the insertion component from the body tissue after insertion of the analytical sensor.

Embodiment 27: The medical system according to any one of the preceding embodiments, wherein the protective cap comprises a plurality of chambers at least partially filled with a desiccant.

Embodiment 28: The medical system according to any one of the preceding embodiments, wherein the medical system further comprises at least one humidity seal received in between the protective cap and the housing.

Embodiment 29: The medical system according to any one of the preceding embodiments, wherein the medical system is contained in a closed package, specifically in a blister pack.

Embodiment 30: A method of manufacturing a medical system, comprising:
 i. providing a housing;
 ii. preassembling a functional module, the preassembled functional module comprising:
  an analytical sensor for detecting at least one analyte in a body fluid of a user;
  an electronics unit electrically connected to the analytical sensor; and
  an insertion component for inserting the analytical sensor into the body tissue;
 iii. receiving the preassembled functional module in the housing; and
 iv. connecting at least one removable protective cap to the housing, thereby covering the preassembled functional module.

Embodiment 31: The method according to the preceding embodiment, wherein the medical system is a medical system according to any one of the preceding embodiments referring to a medical system.

BRIEF DESCRIPTION OF THE FIGURE

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
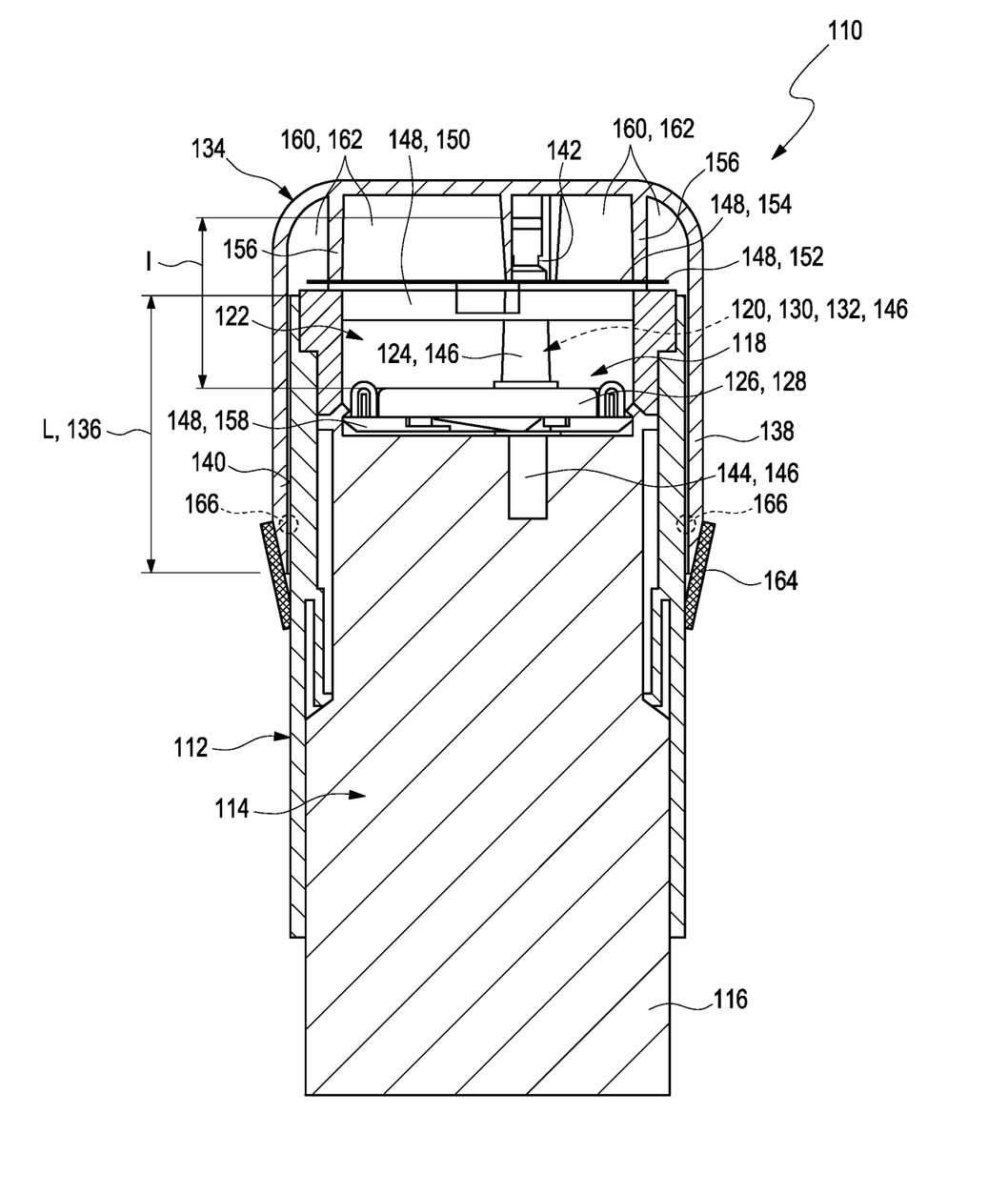
FIG. 1 shows a cross-sectional view of an embodiment of a medical system.

In FIG. 1, a cross-sectional view of an embodiment of a medical system 110 is shown. The medical system comprises a housing 112 which, as an example, may be made of a plastic material. The housing 112 may comprise one component or a plurality of components.

Within the housing 112, in this exemplary embodiment, an insertion actuator 114 is comprised, which, as an example, may comprise a pushbutton 116. As an example for potential details of the insertion actuator, reference may be made to the above-mentioned prior art documents, such as to WO 2017/037191 A1 as well as the prior art cited therein. It shall be noted, however, that other insertion mechanisms are feasible.

Further received within the housing 112 is a preassembled functional module 118. Thus, as an example, the housing 112 may comprise a receptacle 122 in which the preassembled functional module 118 is received. The preassembled functional module 118 comprises an analytical sensor 120 which is not visible in this FIGURE and which is received within a sterility cap 124. The preassembled functional module 118 further comprises at least one electronics unit 126, such as at least one transmitter 128. Further, the preassembled functional module 118 comprises at least one insertion component 130, which also is not visible in this FIGURE. The insertion component 130, as an example, may comprise at least one insertion cannula 132, e.g., an insertion cannula 132 having a slot with the analytical sensor 120 received therein.

The medical system 110 further comprises at least one protective cap 134. The protective cap 134, in the closed state as shown in FIG. 1, which is the state before use of the medical system 110, is connected to the housing 112. Thus, as an example, the protective cap 134 may overlap with the housing 112 in an overlap region 136. Thus, a circumferential rim 138 of the protective cap 134 may snugly fit on a circumferential guiding surface 140 on an upper outer side of the housing 112. The protective cap 134, for disconnecting from the housing 112, may be pulled off from the housing 112, wherein the guiding surface 140 may have a length L in the direction of pulling off the protective cap 134.

When pulling off the protective cap 134 from the housing 112, various functions may be initiated. Thus, as an example, the sterility cap 124 may be connected to the protective cap 134 by a connection 142. Thus, when pulling off the protective cap 134 from the housing 112, the sterility cap 124 may be pulled off from the insertion component 130. Therein, a length l of the sterility cap 124 may be smaller than the guiding length L, such that the sterility cap 124 fully clears the insertion component 130 before the guiding of the protective cap 134 by the guiding surface 140 ends. Thereby, a misplacement of the sterility cap 124 in relation to the insertion component 130 is avoided, which might lead to a damaging of the insertion component 130. Consequently, the connection between the sterility cap 124 and the protective cap 134 may lead to a safe removal of the sterility cap 124 from the insertion component 130.

The sterility cap 124, the insertion component 130 and a holder 144 for the insertion component 130 may form a miniaturized sterile container 146 for the analytical sensor 120. This sterile container 146 may be disassembled, by removing the sterility cap 124, when the protective cap 134 is removed from the housing 112.

The medical system 110 may further comprise a body mount 148. The body mount 148, which may also be placed in the receptacle 122, may contain a cradle 150 which may be placed against the skin of the user once the protective cap 134 is removed. The body mount 148 may further comprise an adhesive plaster 152 on top of the cradle 150, for adhering the cradle 150 onto the skin. The adhesive plaster 152 may be protected by a liner 154 which, e.g., via one or more protrusions 156 of the protective cap 134, may be connected to the protective cap 134. Thus, when the protective cap 134 is removed from the housing 112, the protective cap 134 may also remove the liner 154 from the adhesive plaster 152.

The cradle 150 may be configured for receiving the electronics unit 126. Thus, the electronics unit 126 may also fully or partially be part of the body mount 148. The electronics unit 126, in this exemplary embodiment, may be received in an upper shell 158, which may also form part of the body mount 148 and which may interact with the cradle 150 for providing a cover for the electronics unit 126.

The medical system 110 may further comprise at least one desiccant 160. The desiccant 160 may be comprised in the protective cap 134, specifically in a plurality of chambers 162 provided by the protective cap 134.

The medical system 110 may further comprise at least one indicator seal 164, such as at least one clearly visible tape, at a transition between the protective cap 134 and the housing 112. The indicator seal 164, firstly, may clearly indicate whether the medical system 110 has been used or not and may be broken when removing the protective cap 134 from the housing 112. The indicator seal 164 may provide further functionality, such as by providing a humidity barrier and by preventing or reducing the ingression of humidity into the protective cap 134 and/or into the housing 112. Further, the indicator seal 164 may provide a light barrier and may be rendered light-tight. This is specifically useful in connection with an optical switching mechanism.

Thus, the electronics unit 126 may comprise an optical switch, such as an optical switch having a photodiode or a phototransistor. The protective cap 134 may be light-tight. When removing the protective cap 134 from the housing 112 for the first time, the photosensitive element of the electronics unit 126 may register the ambient light and may switch on the electronics unit 126. Other switches connected to the movement and removal of the protective cap 134 are feasible, such as mechanical switches. Thus, generally, the electronics unit 126 may be configured for being switched on when the protective cap 134 is removed from the housing 112.

For providing further humidity protection, at least one humidity seal 166 may be provided in between the protective cap 134 and the housing. Thus, as an example, one or more lines of glue may be provided on the guiding surface 140.

For use of the medical system 110 according to FIG. 1, the protective cap 134 may be removed from the housing 112. Thereby, as outlined above, the sterility cap 124 may be removed from the insertion component 130. The removal of the sterility cap 124 may take place by purely translational movement, such as in an axial direction in FIG. 1. Additionally or alternatively, the removal of the sterility cap 124 may also imply a rotational movement, e.g., by transforming a translational movement of the protective cap 134 into a rotational movement of the sterility cap 124. Thus, as an example, a connection between the protective cap 134 and the sterility cap 124 may provide for an appropriate motion transformation, e.g., by providing one or more cams.

Further, as outlined above, by removal of the protective cap 134, the liner 154 may be removed, and the electronics unit 126 may be switched on. Subsequent to the removal of the protective cap 134, the housing 112 may be placed onto the desired skin side. Thereby, by the adhesive plaster 152, the cradle 150 is adhered to the skin.

Subsequently, by pushing the push button 116, the insertion component 130, e.g., the insertion cannula 132, is driven into the body tissue, thereby placing the analytical sensor 120 into the body tissue. Once the insertion has taken place, the insertion component 130 is retracted from the body tissue, back into the housing 112, remaining therein and preventing injuries. Further, during the insertion motion initiated by the insertion actuator 114, the body mount 148 is assembled. Thus, the upper shell 158 is connected to the cradle 150, safely placing the electronics unit 126 in between. It shall be noted, however, that the analytical sensor 120 is already electrically connected to the electronics unit 126 in the unused state as shown in FIG. 1, since the functional module 118 is preassembled. Thus, during insertion, no electrical connection between the analytical sensor 120 and the electronics unit 126 has to take place, thereby reducing the complexity of the insertion motion and reducing the risk of electrical failure during the connection. Thus, the electronics unit 126, with the analytical sensor 120 fixedly connected thereto, may fully be designed as a disposable unit, without reusable parts. By providing a battery and by providing a switching mechanism, e.g., triggered by the removal of the protective cap 134, the number of handling steps may significantly be reduced, leading to a simplified operating procedure which can be managed even by elderly people and children.

After insertion of the analytical sensor 120 into the body tissue and placement of the body mount 148 onto the skin, the remaining parts of the medical system 110, specifically the housing 112 and the insertion actuator 114, may be removed and may be disposed of No further handling steps are required for the user, e.g., no further handling steps such as connecting electronic components to the analytical sensor 120 and/or the body mount 148 or the electronics unit 126. Thus, after performing the above-mentioned steps, without further steps, the analytical sensor 120 and the electronics unit 126 may provide measurement values. The measurement values, as an example, may be transmitted wirelessly to a receiver, such as a medical data management system.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 medical system
112 Housing
114 insertion actuator
116 Pushbutton
118 preassembled functional module
120 analytical sensor
122 Receptacle
124 sterility cap
126 electronics unit
128 Transmitter
130 insertion component
132 insertion cannula
134 protective cap
136 overlap region
138 Rim
140 guiding surface
142 Connection
144 Holder
146 sterile container
148 body mount
150 Cradle
152 adhesive plaster
154 Liner
156 Protrusion
158 upper shell
160 Desiccant
162 Chamber
164 indicator seal
166 humidity seal

What is claimed is:

1. A medical system, comprising:
a housing having an outer surface;
a protective cap removably connected to the housing, the protective cap having an inner surface that overlaps the outer surface of the housing by a length L;
a module, comprising:
an electronics unit electrically connected to an analyte sensor for detecting an analyte in a body fluid of a user;
an insertion cannula in which the analyte sensor is at least partially received, the insertion cannula configured for inserting the analyte sensor into body tissue of the user; and
a sterile container containing at least part of the analyte sensor and at least part of the insertion cannula in a sterile environment, the sterile container comprising a sterility cap that seals off the sterile environment, further wherein the sterility cap is inside the protective cap when the protective cap is connected to the housing and wherein the sterility cap has a length I, and L is greater than 1, whereby the sterility cap is fully removed from the insertion cannula before completion of the cooperating of the outer surface with the inner surface during the removing of the protective cap from the housing;
wherein the sterility cap is connected to the protective cap and removing the protective cap from the housing removes the sterility cap from the sterile container and exposes the insertion cannula for insertion into the body tissue;
wherein the outer surface of the housing cooperates with the inner surface of the protective cap over the length L to guide the sterility cap axially during the removing of the protective cap from the housing until the sterility cap clears the insertion cannula, whereby the risk of damaging the insertion cannula during the removing of the sterility cap is reduced.

2. The medical system according to claim 1, wherein the outer surface of the housing faces the inner surface of the protective cap.

3. The medical system according to claim 2, wherein the removing of the protective cap from the housing comprises a movement selected from the group consisting of:
a translational movement of the protective cap and the sterility cap when the protective cap is removed from the housing;
a rotational movement of the protective cap and the sterility cap when the protective cap is removed from the housing;
both a translational and a rotational movement of the protective cap and the sterility cap when the protective cap is removed from the housing.

4. The medical system according to claim 3, wherein the removing of the protective cap from the housing includes both the translational and rotational movements of the protective cap and the sterility cap.

5. The medical system according to claim 4, wherein the sterility cap is connected to the module by a bayonet connection, wherein, by the rotational movement, the bayonet connection is untightened and the sterility cap is removable from the module.

6. The medical system according to claim 1, wherein, when the protective cap is removed from the housing, the protective cap performs a translational movement along a longitudinal axis of the medical device and an additional rotational movement.

7. The medical system of claim 6, wherein the rotational movement comprises a threaded engagement between the housing and the protective cap.

8. The medical system according to claim 1, further comprising an indicator seal connected to the protective cap and the housing, wherein the indicator seal is configured to be broken when the protective cap is removed from the housing.

9. The medical system according to claim 1, further comprising an insertion actuator configured for advancing the insertion cannula after the removing of the protective cap from the housing and for inserting the analyte sensor into the body tissue.

10. The medical system according to claim 9, wherein the electronics unit has an opening through which the insertion cannula protrudes, wherein the insertion actuator drives the insertion cannula through the opening during an insertion operation.

11. The medical system according to claim 1, wherein the sterility cap remains connected to the protective cap when the protective cap is removed from the housing.

12. The medical system according to claim 11, wherein the removing of the protective cap from the housing causes a rotational movement of the sterility cap.

13. The medical system according to claim 12, wherein the removing of the protective cap from the housing causes rotational movements of the sterility cap and protective cap about a common axis.

14. The medical system according to claim 13, wherein, during the removing of the protective cap from the housing, the sterility cap is guided axially along the common axis until the sterility cap clears the insertion cannula.

15. The medical system according to claim 1, wherein the sterility cap is connected to the module by a bayonet connection, wherein a rotational movement of the sterility cap allows the removing of the sterility cap from the module.

16. The medical system according to claim 1, wherein the protective cap and the sterility cap are made of different materials.

17. The medical system according to claim 1, wherein the housing has a front face configured for contacting skin of the user, wherein the front face has an opening enclosed by a rim, wherein the rim is configured for tightening the skin before insertion of the analyte sensor.

18. The medical system according to claim 1, wherein the module comprises at least one guiding surface for guiding the sterility cap during the removing of the sterility cap.

19. The medical system according to claim 1, wherein the electronics unit comprises at least one electronics unit housing, wherein the analyte sensor protrudes into the electronics unit housing and is electrically connected with at least one electronic component within the electronics unit housing.

20. The medical system according to claim 1, wherein the medical system comprises a switching mechanism configured to switch on the electronics unit.

21. The medical system according to claim 1, wherein the electronics unit is switched on after the protective cap is removed from the housing.

22. The medical system according to claim 1, wherein the protective cap is connected to the housing by a form-fit, a force fit or a threaded connection.

23. The medical system according to claim 1, further comprising a receptacle in the housing for receiving the module, wherein the receptacle is located in a front face of the housing and is fully or partially surrounded by a frame formed by the housing.

24. The medical system according to claim 23, wherein the receptacle is covered by the protective cap and the module is accessible when the protective cap is removed from the housing.

25. The medical system according to claim 1, wherein the housing, the module and the protective cap form a pre-assembled single unit.

26. The medical system according to claim 1, wherein the analyte sensor is an electrochemical analyte sensor.

27. The medical system according to claim 1, wherein the insertion cannula further comprises at least one holder for the insertion cannula, wherein the holder, the insertion cannula and the sterility cap form components of the sterile container for the analyte sensor.

28. The medical system according to claim 27, wherein the sterility cap is connected to the protective cap via one or more guiding elements for transforming a movement of the protective cap into a desired movement of the sterility cap, wherein the sterility cap is unlockable from the holder by a bayonet lock.

29. The medical system according to claim 27, wherein the holder comprises a rigid component connected to a proximal end of the insertion cannula.

30. The medical system according to claim 1, wherein the module comprises a factory pre-assembled module.

31. The medical system according to claim 30, wherein in the pre-assembled module, the electronics unit and the analyte sensor are already connected.

32. The medical system according to claim 1, wherein the housing, the module and the protective cap form a single factory assembled unit.

33. The medical system according to claim 32, wherein the single factory assembled unit is packaged.

34. The medical system according to claim 1, wherein the electronics unit is irreversibly connected to the analyte sensor.

35. The medical system according to claim 1, wherein the outer surface of the housing slides against the inner surface of the protective cap when the protective cap is removed from the housing.

* * * * *